United States Patent
Benzel et al.

(10) Patent No.: US 7,588,600 B2
(45) Date of Patent: Sep. 15, 2009

(54) METHOD FOR REPLACING A DAMAGED SPINAL DISC

(75) Inventors: Edward C. Benzel, Gates Mills, OH (US); Isador H. Lieberman, Pepper Pike, OH (US); Lee Strnad, Broadview Heights, OH (US); James M. Kuras, Macedonia, OH (US); Raymond S. Ross, Sale (GB); Charles F. Birchall, Jr., Mentor, OH (US); Keith Duke, Cleveland, OH (US); Kari Zimmers, Solon, OH (US)

(73) Assignee: Axiomed Spine Corporation, Beachwood, OH (US)

( * ) Notice: Subject to any disclaimer, the term of this patent is extended or adjusted under 35 U.S.C. 154(b) by 956 days.

(21) Appl. No.: 10/731,942

(22) Filed: Dec. 10, 2003

(65) Prior Publication Data

US 2005/0131542 A1    Jun. 16, 2005

(51) Int. Cl.
*A61F 2/44* (2006.01)
(52) U.S. Cl. .............. 623/17.15; 623/17.11; 623/17.16; 606/279
(58) Field of Classification Search ............... 606/61, 606/279; 623/17.11–17.16
See application file for complete search history.

(56) References Cited

U.S. PATENT DOCUMENTS

| | | | |
|---|---|---|---|
| 4,309,777 A | | 1/1982 | Patil |
| 4,573,469 A | * | 3/1986 | Golden et al. ............... 606/220 |
| 4,843,927 A | * | 7/1989 | Gulistan ........................ 81/416 |
| 4,863,477 A | | 9/1989 | Monson ........................ 623/17 |

(Continued)

FOREIGN PATENT DOCUMENTS

EP    1285632    2/2003

(Continued)

OTHER PUBLICATIONS

Lego, <http://web.archive.org/web/20000510061922/http://lego.com/>, accessed Nov. 19, 2007.*

(Continued)

*Primary Examiner*—Eduardo C Robert
*Assistant Examiner*—Julianna N Harvey
(74) *Attorney, Agent, or Firm*—Tarolli, Sundheim, Covell & Tummino LLP

(57) ABSTRACT

A method for replacing a damaged spinal disc between first and second vertebrae of a spinal column includes connecting a first mounting member with the first vertebra of the spinal column. An artificial disc is moved between the first and second vertebrae and into engagement with the first mounting member to guide the artificial disc into position between the first and second vertebrae. The artificial disc includes a resilient core having a first surface and a second surface, a first retaining member connected to the first surface of the resilient core, and a second retaining member connected to the second surface of the resilient core. The first retaining member has an outer surface engageable with a first vertebra of the spinal column and an inner surface facing the first surface of the resilient core. The second retaining member has an outer surface engageable with the second vertebra of the spinal column and an inner surface facing the second surface of the resilient core.

39 Claims, 10 Drawing Sheets

U.S. PATENT DOCUMENTS

| | | | |
|---|---|---|---|
| 4,874,389 A | 10/1989 | Downey | |
| 4,911,718 A | 3/1990 | Lee et al. | 623/17 |
| 4,932,969 A | 6/1990 | Frey et al. | 623/17 |
| 5,123,926 A | 6/1992 | Pisharodi | |
| 5,314,477 A * | 5/1994 | Marnay | 623/17.15 |
| 5,320,644 A | 6/1994 | Baumgartner | 623/17 |
| 5,370,697 A | 12/1994 | Baumgartner | 623/17 |
| 5,401,269 A * | 3/1995 | Buttner-Janz et al. | 623/17.15 |
| 5,545,229 A | 8/1996 | Parsons et al. | 623/17 |
| 5,556,431 A | 9/1996 | Buttner-Janz | |
| 5,571,109 A | 11/1996 | Bertagnoli | 606/61 |
| 5,584,887 A * | 12/1996 | Kambin | 606/914 |
| 5,674,294 A | 10/1997 | Bainville et al. | 623/17 |
| 5,676,702 A | 10/1997 | Ratron | 623/17 |
| 5,824,094 A | 10/1998 | Serhan et al. | 623/17 |
| 5,893,889 A * | 4/1999 | Harrington | 623/17.16 |
| 6,086,613 A | 7/2000 | Camino et al. | |
| 6,113,638 A | 9/2000 | Williams et al. | 623/17 |
| 6,156,067 A * | 12/2000 | Bryan et al. | 623/17.15 |
| 6,231,609 B1 | 5/2001 | Mehdizadeh | 623/17.11 |
| 6,280,446 B1 * | 8/2001 | Blackmore | 606/74 |
| 6,296,664 B1 | 10/2001 | Middleton | 623/17.15 |
| 6,368,350 B1 | 4/2002 | Erickson et al. | |
| 6,402,785 B1 | 6/2002 | Zdeblick et al. | |
| 6,419,706 B1 | 7/2002 | Graf | 623/17.16 |
| 6,454,806 B1 | 9/2002 | Cohen et al. | 623/17.15 |
| 6,533,818 B1 | 3/2003 | Weber et al. | 623/17.16 |
| 6,607,558 B2 | 8/2003 | Kuras | 623/17.16 |
| 7,060,097 B2 | 6/2006 | Fraser et al. | |
| 7,128,761 B2 | 10/2006 | Kuras et al. | |
| 2001/0016774 A1 | 8/2001 | Bresina et al. | 623/17.15 |
| 2002/0116009 A1 | 8/2002 | Fraser et al. | 606/99 |
| 2002/0143333 A1 * | 10/2002 | von Hoffmann et al. | 606/67 |
| 2002/0161446 A1 | 10/2002 | Bryan et al. | |
| 2002/0183757 A1 * | 12/2002 | Michelson | 606/71 |
| 2003/0045939 A1 | 3/2003 | Casutt | 623/17.15 |
| 2003/0074071 A1 | 4/2003 | Errico et al. | 623/17.14 |
| 2003/0074076 A1 | 4/2003 | Ferree et al. | 623/17.16 |
| 2003/0187506 A1 * | 10/2003 | Ross et al. | 623/17.13 |
| 2004/0122517 A1 | 6/2004 | Kuras | |
| 2006/0178744 A1 | 8/2006 | Devilliers et al. | |

FOREIGN PATENT DOCUMENTS

| | | |
|---|---|---|
| JP | 04106035 | 3/1992 |
| WO | 9113598 | 9/1991 |
| WO | WO-95/26697 A1 | 10/1995 |
| WO | 02089701 | 11/2002 |

OTHER PUBLICATIONS

"Physical Properties and Functional Biomechanics of the Spine", Chapter 1, pp. 1-19 and Reference pp. 77-83.

"Requirements for an Artificial Intervertebral Disc", Chapter 2, by Eijkelkamp, et al., pp. 25-42.

"Mechanical Properties of Human Lumbar Spine Motion Segments Part II: Responses in Compression and Shear Influence of Gross Morphology", by Berkson, et al., Journal of Biomechanical Engineering Feb. 1979, vol. 101 pp. 53-57.

"Some Static Mechanical Properties of the Lumbar Intervertebral Joint, Intact and Injured", by Tencer, et al., Journal of Biomechanical Engineering, Aug. 1982, vol. 104, pp. 193-201.

"Variation of Lumbar Spine Stiffness with Load", by Edwards, et al., Journal of Biomechanical Engineering, Feb. 1987, vol. 109, pp. 35-42.

"Limitations of the Standard Linear Solid Model of Intervertebral Discs Subject To Prolonged Loading And Low-Frequency Vibration In Axial Compression", by Li, et al., J. Biomechanics, vol. 28, No. 7 pp. 779-790, 1995.

Benzel et al. U.S. Appl. No. 10/731,964, filed Dec. 10, 2003 entitled "Method and Apparatus for Replacing a Damaged Spinal Disc".

Kuras et al. U.S. Appl. No. 10/732,660, filed Dec. 10, 2003 entitled "Method and Apparatus for Replacing a Damaged Spinal Disc".

\* cited by examiner

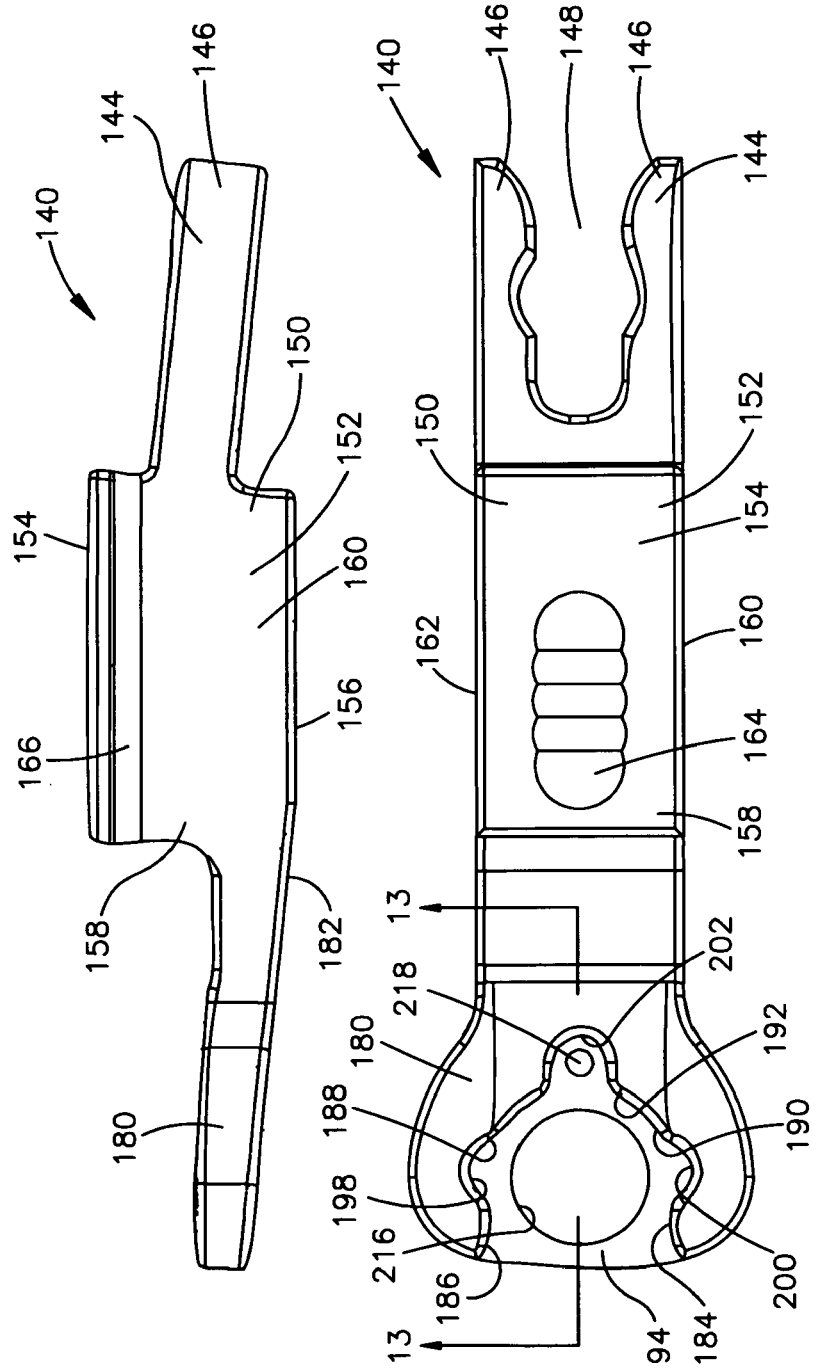

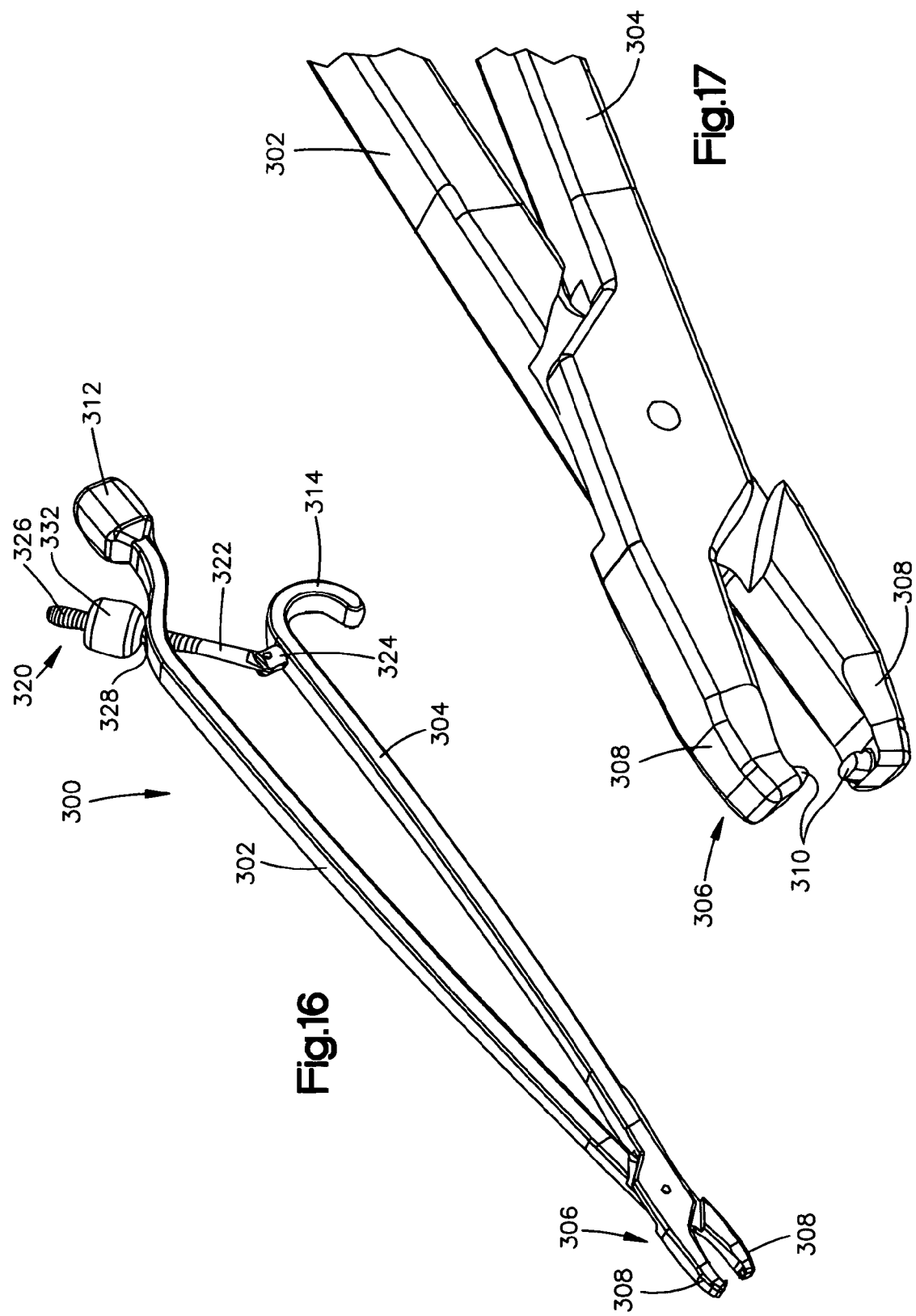

US 7,588,600 B2

METHOD FOR REPLACING A DAMAGED SPINAL DISC

FIELD OF THE INVENTION

The present invention relates to a method and an apparatus for replacing a damaged spinal disc in a spinal column, and more specifically, to an apparatus having a resilient core for replacing a damaged spinal disc in a spinal column.

BACKGROUND OF THE INVENTION

A known artificial disc member is disclosed in U.S. Pat. Nos. 5,370,697. 5,370,697 discloses an artificial disc having upper and lower supports connected to adjacent vertebrae and an elastic separator. The separator has cover plates connected to opposite sides of an elastic core. The separator is a separate insert part that may be inserted between the upper and lower supports after the supports are connected to the vertebrae. The separator does not engage the vertebrae.

SUMMARY OF THE INVENTION

A method for replacing a damaged spinal disc between first and second vertebrae of a spinal column includes connecting a first mounting member with the first vertebra of the spinal column. An artificial disc is moved between the first and second vertebrae and into engagement with the first mounting member to guide the artificial disc into position between the first and second vertebrae. The artificial disc includes a resilient core having a first surface and a second surface, a first retaining member connected to the first surface of the resilient core, and a second retaining member connected to the second surface of the resilient core. The first retaining member has an outer surface engageable with a first vertebra of the spinal column and an inner surface facing the first surface of the resilient core. The second retaining member has an outer surface engageable with the second vertebra of the spinal column and an inner surface facing the second surface of the resilient core.

BRIEF DESCRIPTION OF THE DRAWINGS

The foregoing and other features of the present invention will become apparent to one skilled in the art to which the present invention relates upon consideration of the following description of the invention with reference to the accompanying drawings, in which:

FIG. 11 is a schematic side view of the insertion member of FIG. 10;

FIG. 12 is a schematic top view of the insertion member of FIG. 10;

FIG. 13 is a sectional view of a portion of the insertion member taken along the line 13-13 in FIG. 12;

FIG. 16 is a pictorial view of a surgical tool for use in inserting the artificial disc of FIG. 2 between the adjacent vertebrae; and FIG. 17 is an enlarged view of a portion of the surgical tool of FIG. 16.

DESCRIPTION OF THE INVENTION

Figure 1:
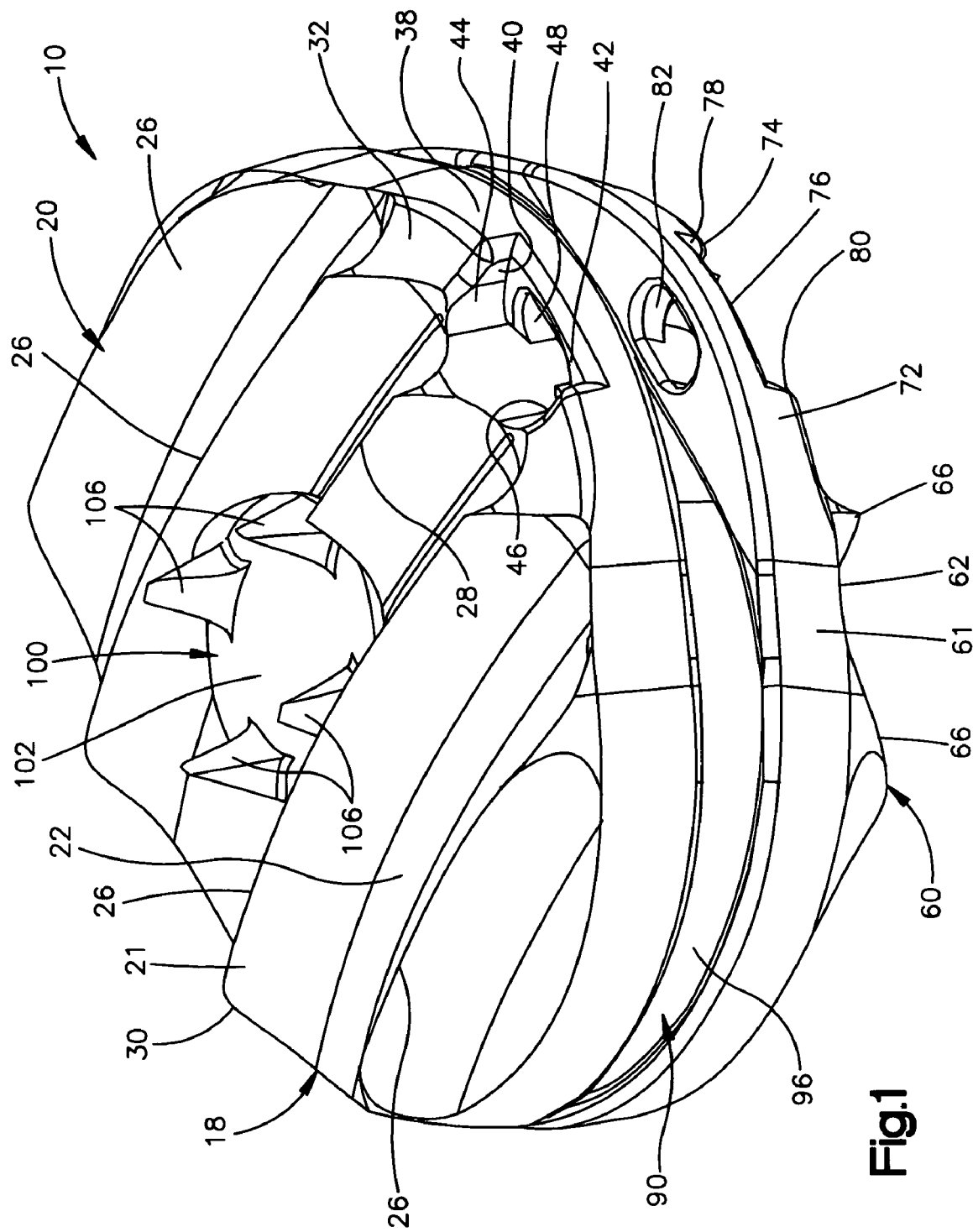
FIG. 1 is a pictorial view of an apparatus to replace a damaged spinal disc constructed in accordance with the present invention.
Figure 2:
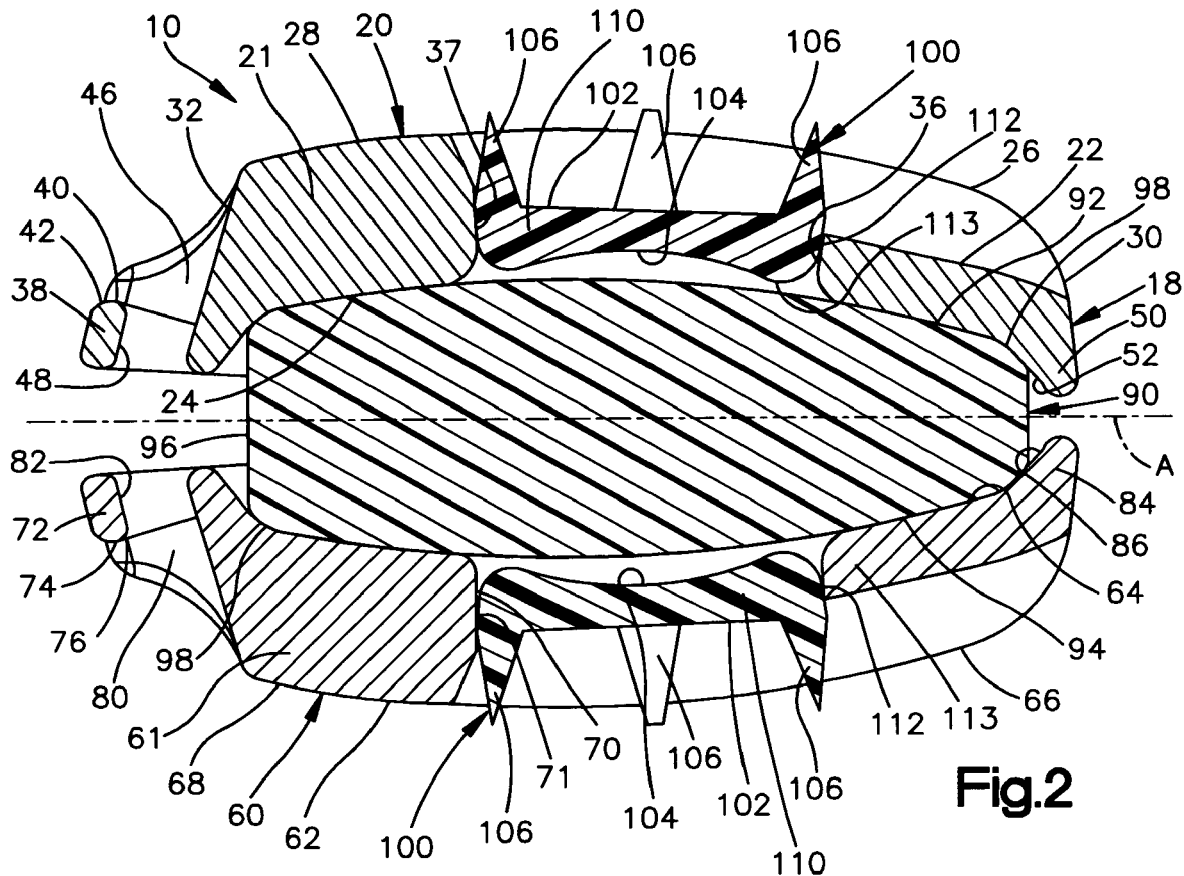
FIG. 2 is a sectional view of the apparatus of FIG. 1.

The present invention relates to an apparatus or prosthesis to replace a damaged or degenerated spinal disc in a spinal column of a human. FIGS. 1-7 illustrate an apparatus or prosthesis 10 to replace a damaged or degenerated spinal disc in a spinal column. The apparatus 10 (FIG. 6) is used to replace a damaged spinal disc between adjacent upper and lower vertebrae 12 and 14 of a human spinal column 16. The apparatus 10 (FIGS. 1-7) includes an artificial disc 18 and mounting members 100 that help connect the disc 18 to the adjacent vertebrae 12 and 14. The mounting members 100 also help position the disc 18 relative to the vertebrae 12 and 14.

Figure 3:
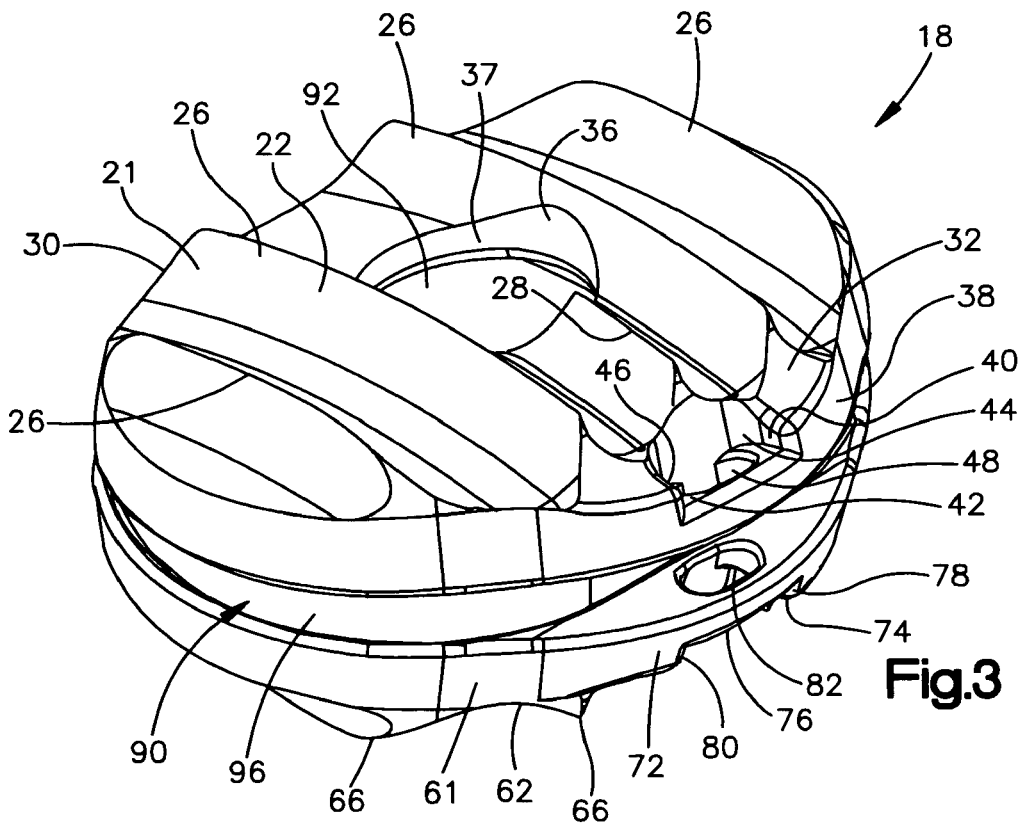
FIG. 3 is a pictorial view of an artificial disc of the apparatus of FIG. 1
Figure 4:
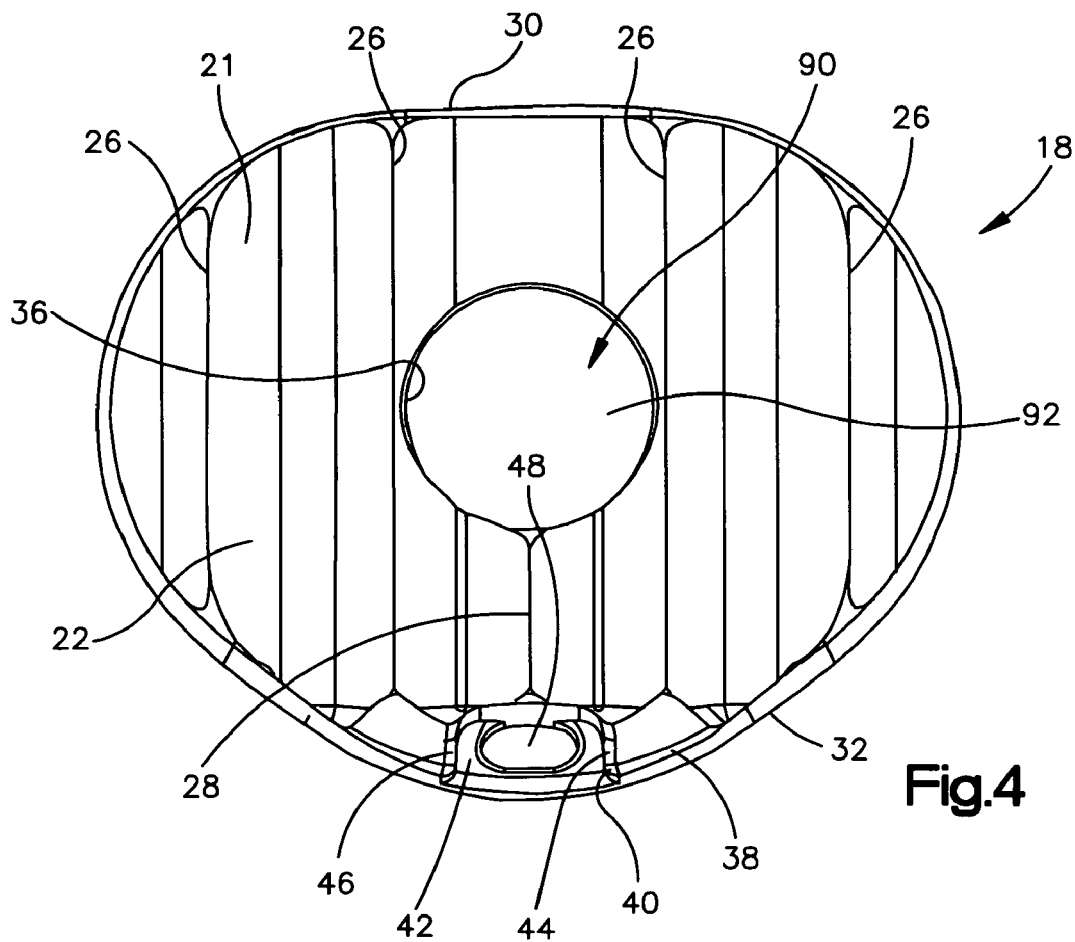
FIG. 4 is a schematic top view of the artificial disc of FIG. 3.
Figure 6:
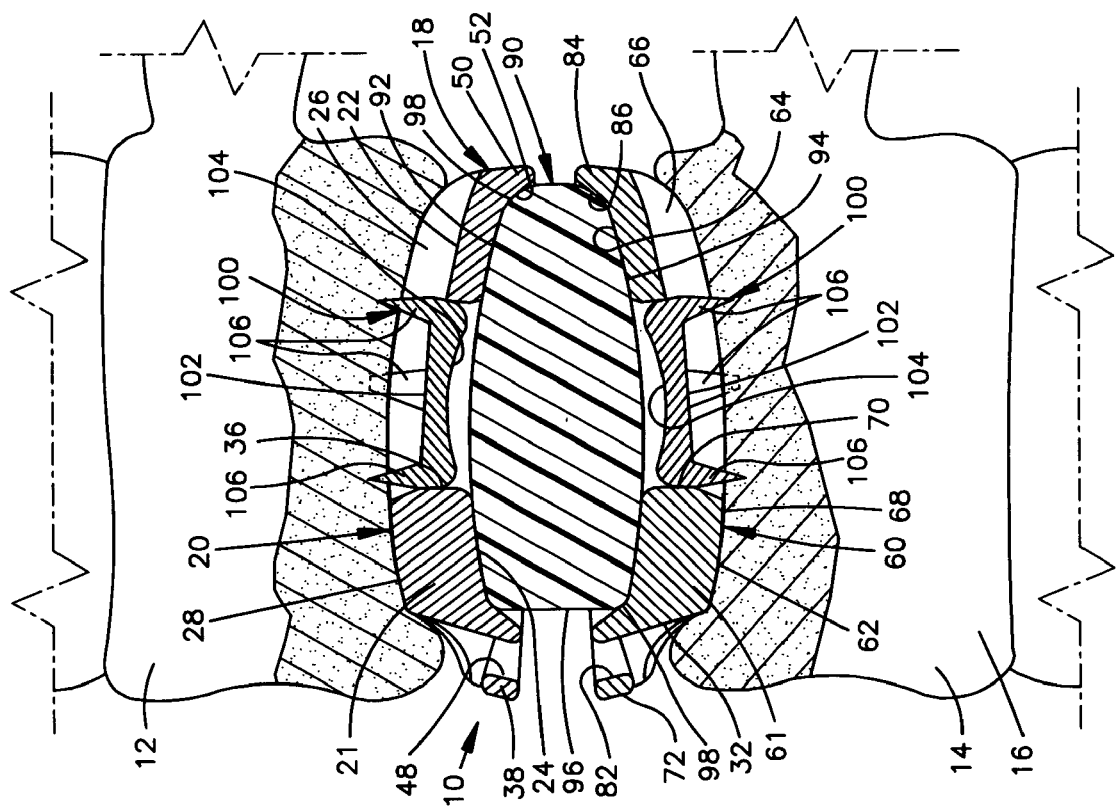
FIG. 6 is a schematic sectional view of the apparatus of FIG. 1 between adjacent vertebrae of a human spinal column.

The apparatus 10 (FIG. 1) includes an upper or first retaining device 20, a lower or second retaining device 60 and a resilient core 90 interposed between and adhered to the retaining devices. The upper and lower retaining devices 20 and 60 are identical to each other and include mounting members 100. The apparatus 10 is symmetrical about a horizontally extending plane A (FIG. 3). The terms "upper" and "lower" are used herein with reference to the orientation of the apparatus 10 when in the human body, as illustrated in FIG. 6, to distinguish the two identical retaining devices for reference purposes.

The upper retaining device 20 includes an upper or first retaining ring or member 21 and a mounting member 100. The artificial disc 18 includes the upper retaining member 21. The upper retaining member 21 is rigid and made of a biocompatible material such as a biocompatible metal or polymer. It is contemplated that the upper retaining member 21 could be made of a titanium alloy. The upper retaining member 21 has an outer surface 22 engageable with the vertebra 12. An inner concave surface 24 of the upper retaining member 21 is affixed or bonded to the resilient core 90. It is contemplated that the inner surface 24 may have beads (not shown) sintered on the inner surface or a texture (not shown) etched onto the inner surface to help connect the upper retaining member 21 to the core 90.

Figure 7:
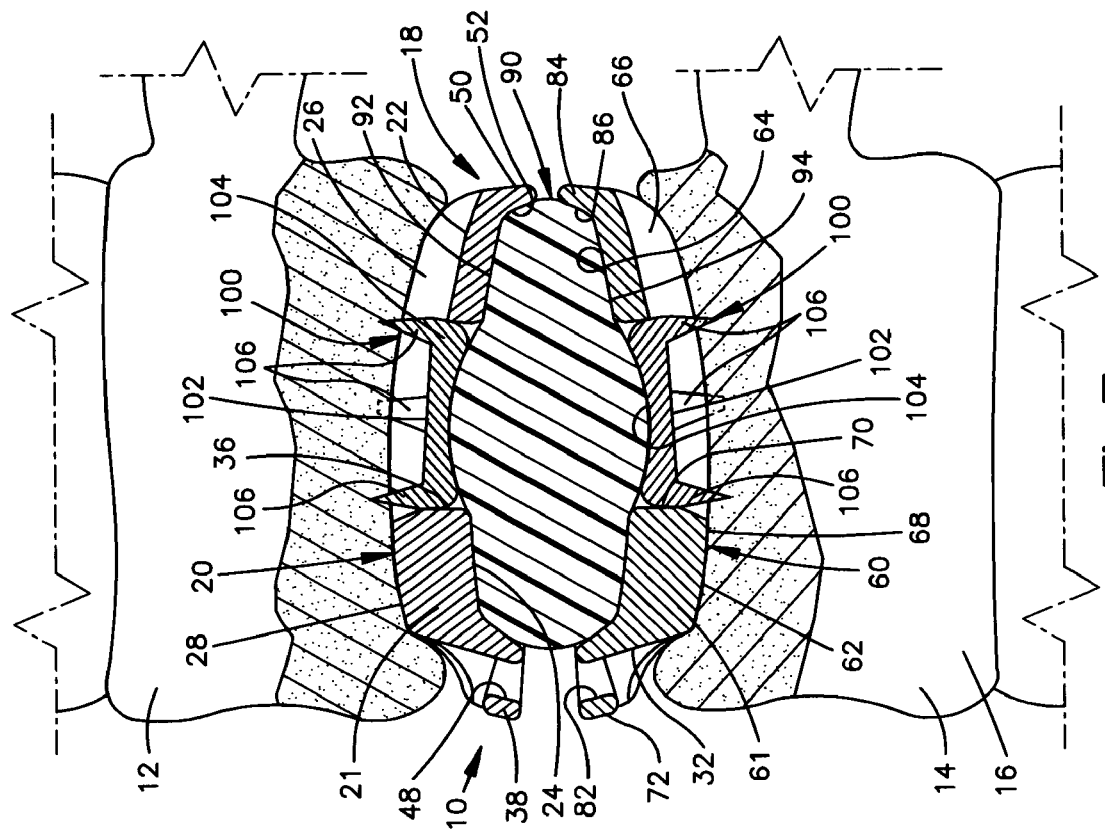
FIG. 7 is a schematic sectional view of the apparatus of FIG. 1 between adjacent vertebrae of the spinal column showing the spinal column in compression.

A plurality of guides or ribs 26 (FIGS. 3-4) and a central rib 28 extend from the outer surface 22. Although the upper retaining member 21 is shown as having four ribs 26, it is contemplated that the upper retaining member may have any number of ribs 26. The ribs 26 engage the vertebra 12, as shown in FIGS. 6-7, to retain the apparatus 10 in position between the vertebrae 12 and 14. The outer surface 22 may also have beads (not shown) sintered on the outer surface or a texture (not shown) etched onto the outer surface to further retain the apparatus 10 between the vertebrae 12 and 14.

The ribs 26 (FIGS. 1-4) extend generally parallel to each other from a proximal side 30 of the disc 18 to an anterior side 32 of the disc. The central rib 28 extends from the anterior side 32 of the disc 18 to an axially extending circular opening 36 in the upper retaining member 21. It is contemplated that the ribs 26 and 28 may extend in any desired direction. The direction in which the ribs 26 and 28 extend is determined by the direction of insertion of the disc 18.

The axially extending opening 36 (FIGS. 2-4) extends through the outer surface 22 and the inner surface 24 of the upper retaining member 21. The upper retaining member 21 has a frustoconical surface 37 at least partially defining the opening 36. An upper portion of the opening 36 has a first diameter and a lower portion of the opening has a second diameter smaller than the first diameter. The opening 36 is centrally located between two of the ribs 26. Accordingly, there is no rib extending from the proximal side 30 of the disc 18 to the opening 36. Although the opening 36 is shown as being circular, it is contemplated that the opening may have any desired shape.

A flange portion 38 extends from the upper retaining member 21 on the anterior side 32 of the disc 18. The flange portion 38 has a recess 40 adjacent the central rib 28. The recess 40 is defined by a bottom surface 42 and side surfaces 44 and 46 extending upwardly from the bottom surface 42. An oval shaped slot 48 extends through the bottom surface 42 of the flange portion 38. The slot 48 extends in a direction transverse to the direction in which the rib 28 extends.

The inner concave surface 24 (FIG. 2) of the upper retaining member 21 is affixed or bonded to the resilient core 90. The upper retaining member 21 includes a peripheral flange portion 50 extending toward the lower retaining device 60. The flange 50 encircles the core 90. The flange 50 has a radially inner surface 52 facing the core 90. The surface 52 extends radially outwardly from the concave surface 24 and toward the lower retaining device 60. The surface 52 on the flange 50 is spaced from the core 90, as shown in FIG. 6, until a predetermined load is applied to the apparatus 10.

The core 90 deflects toward the surface 52 on the flange 90 when a load is applied to the apparatus 10 to move the upper and lower retaining devices 20 and 60 relative to each other. When the predetermined load is applied to the apparatus 10, as shown in FIG. 7, the core 90 deflects into engagement with the surface 52 on the flange 50. When the core 90 engages the flange 50, the core stiffens since further deflection of the core is restricted by the flange 50.

The surface 52 of the flange 50 may have any desired configuration. The surface 52 may have a first portion that extends closer to the core 90 than a second portion so that the core engages the first portion of the surface 52 prior to engaging the second portion of the surface 52. Accordingly, the core 90 may engage different portions of the surface 52 as different loads are applied to the apparatus 10 to vary the stiffness of the core at the different loads.

It is contemplated that the retaining member 21 may have an inner surface (not shown) extending from the concave inner surface 24 to the opening 36 and spaced from the core 90 until a predetermined load is applied to the apparatus 10. When the predetermined load is applied to the apparatus 10, the core 90 deflects into engagement with the inner surface (not shown) extending from the concave surface 24 to the opening 36. When the core 90 engages the inner surface extending from the concave surface 24 to the opening 36, the core stiffens since further deflection of the core is restricted by the retaining member 21.

The lower retaining device 60 (FIGS. 1-2) is identical in configuration to the upper retaining device 20. The lower retaining device 60 includes a lower or second retaining member or ring 61 and a mounting member 100. The disc 18 includes the lower retaining member 61. The lower retaining member 61 is identical to the upper retaining member 21. Accordingly, the lower retaining member 61 will not be described in detail. The lower retaining member 61 is rigid and made from the same material as the upper retaining member 21, such as a titanium alloy. The lower retaining member 61 has an outer surface 62 engageable with the vertebra 14. An inner concave surface 64 of the lower retaining member 61 is affixed or bonded to the resilient core 90. It is contemplated that the inner surface 64 may have beads (not shown) sintered on the inner surface or a texture (not shown) etched onto the inner surface to help connect the lower retaining member 61 to the core 90.

A plurality of guides or ribs 66 (FIGS. 2 and 3) and a central rib 68 extend from the outer surface 62. The lower retaining member 61 may have any number of ribs 66. The ribs 66 engage the vertebra 14, as shown in FIGS. 6 and 7, to retain the apparatus 10 in position between the vertebrae 12 and 14. The outer surface 62 may also have beads (not shown) sintered on the outer surface or a texture (not shown) etched onto the outer surface to further retain the apparatus 10 between the vertebrae 12 and 14.

The ribs 66 extend generally parallel to each other from the proximal side 30 of the disc 18 to the anterior side 32. The central rib 68 (FIG. 2) extends from the anterior side 32 to an axially extending circular opening 70 in the lower retaining member 61. It is contemplated that the ribs 66 and 68 may extend in any desired direction. The direction in which the ribs 66 and 68 extend is determined by the direction of insertion of the disc 18.

The axially extending opening 70 (FIG. 2) extends through the outer surface 62 and the inner surface 64 of the upper retaining member 61. The lower retaining member 61 has a frustoconical surface 71 at least partially defining the opening 70. A lower portion of the opening 70 has a first diameter and an upper portion of the opening has a second diameter smaller than the first diameter. The opening 70 is centrally located between two of the ribs 66. Accordingly, there is no rib extending from the proximal side 30 of the disc 18 to the opening 70. Although the opening 70 is described as being circular, it is contemplated that the opening may have any desired shape.

A flange portion 72 extends from the lower retaining member 61 on the anterior side 32 of the disc 18. The flange portion 72 has a recess 74 adjacent the central rib 68. The recess 74 is defined by an upper surface 76 and side surfaces 78 and 80 extending downwardly from the upper surface 76. An oval shaped slot 82 extends through the upper surface 76 of the flange portion 72. The slot 82 extends in a direction transverse to the direction in which the central rib 68 extends.

The inner concave surface 64 (FIG. 2) of the lower retaining member 61 is affixed or bonded to the resilient core 90. The lower retaining member 61 includes a peripheral flange portion 84 extending toward the upper retaining device 20. The flange 84 encircles the core 90. The flange 84 has a radially inner surface 86 facing the core 90. The surface 86 extends radially outwardly from the concave surface 64 and toward the upper retaining device 20. The surface 86 on the flange 84 is spaced from the core 90, as shown in FIG. 6, until a predetermined load is applied to the apparatus 10.

The core 90 deflects toward the surface 86 on the flange 84 when a load is applied to the apparatus 10 to move the upper and lower retaining devices 20 and 60 relative to each other. When a predetermined load is applied to the apparatus 10, as shown in FIG. 7, the core 90 deflects into engagement with the surface 86 on the flange 84. When the core 90 engages the flange 84, the core stiffens since further deflection of the core is restricted by the flange 84.

The surface 86 of the flange 84 may have any desired configuration. The surface 86 may have a first portion that extends closer to the core 90 than a second portion so that the core engages the first portion of the surface 86 prior to engaging the second portion of the surface 86. Accordingly, the core 90 may engage different portions of the surface 86 as different loads are applied to the apparatus 10 to vary the stiffness of the core at different loads. It is also contemplated that the flange 84 on the lower retaining member 61 may engage the flange 50 on the upper retaining member 21 when a predetermined load is applied to the apparatus 10.

It is contemplated that the retaining member 61 may have an inner surface (not shown) extending from the concave inner surface 64 to the opening 70 and spaced from the core 90 until a predetermined load is applied to the apparatus 10. When the predetermined load is applied to the apparatus 10, the core 90 deflects into engagement with the inner surface (not shown) extending from the concave surface 64 to the opening 70. When the core 90 engages the inner surface extending from the concave surface 64 to the opening 70, the core stiffens since further deflection of the core is restricted by the retaining member 61.

The resilient core 90 is one-piece and may be made of a urethane silicone blend manufactured by the Polymer Technology Group located in Berkley, Calif. The resilient core 90 may be adhered or bonded to the upper and lower retaining members 21 and 61 in any manner known in the art. It is contemplated that the resilient core 90 could be insert molded, transfer molded or injection molded between the upper and lower retaining members 21 and 61. The core 90 may be molded between the upper and lower retaining members 21 and 61 by injecting the material for the core through one of the openings 36 or 70 in the upper and lower retaining members.

The resilient core 90 may be made of a polymer that is a silicone-polycarbonate-urethane copolymer by the name of CarboSil™ manufactured by the Polymer Technology Group located in Berkley, Calif. The resilient core 90 is prepared through a multi-step bulk synthesis during which polydimethylsiloxane is incorporated into the polymer soft segment with aliphatic, hydroxyl-terminated polycarbonate oligomers. The hard segment consists of an aromatic diisocyanate with a low molecular weight glycol chain extender. The copolymer chains are terminated with silicone.

The material of the resilient core 90 combines the biocompatibility and biostability of silicone elastomers with the processibility and toughness of thermoplastic urethane elastomers. The material of the resilient core 90 has a relatively high hard segment content that softens significantly upon reaching equilibrium with the body of a patient. The relevant equilibrium involves thermal equilibrium with the body at approximately 37° C. and equilibrium water and solute uptake by the polymer after being implanted in the body. The material of the resilient core 90 has a decreased modulus at 37° C. compared to that at room temperature. Accordingly, the higher durometer polymer can be used for its biostability, since conditions in the human body lower the modulus of the polymer to the desired range of compressive stiffness.

The resilient core 90 is wedge shaped. The upper retaining member 21 is spaced from the lower retaining member 61 a first distance adjacent the proximal side 30 of the disc 18. The upper retaining member 21 is spaced from the lower retaining member 61 a second distance greater than the first distance adjacent the anterior side 32 of the disc 18. It is contemplated that the upper retaining member 21 may be spaced from the lower retaining member 61 by any desired distances.

The core 90 has an upper or first convex surface 92. The upper convex surface 92 is affixed to the concave inner surface 24 of the upper retaining member 21. A lower or second convex surface 94 is affixed to the concave inner surface 64 of the lower retaining member 61.

The core 90 includes a radially outer surface 96. Arcuate transition surfaces 98 extend between the radially outer surface 96 and the upper and lower surfaces 92 and 94. The radially outer surface 96 is spaced from the flanges 50 and 84 on the upper and lower retaining members 21 and 61 until the predetermined load is applied to the apparatus 10.

The peripheral surface 96 and the transition surfaces 98 may have any desired configuration. The surfaces 96 and 98 may have first portions that extend closer to the flanges 50 and 84 than second portions so that the first portions engage the flanges 50 and 84 prior to the second portions. Accordingly, the different portions of the surfaces 96 and 98 may engage the flanges 50 and 84 as different loads are applied to the apparatus 10 to vary the stiffness of the core 90 at different loads.

Each of the retaining devices 20 and 60 (FIGS. 1-7) includes a mounting member 100 to help connect the disc 18 to the vertebrae 12 and 14. The mounting members 100 also help position the disc 18 between the vertebrae 12 and 14. The mounting members 100 (FIG. 6) extend into the openings 36 and 70 in the retaining members 21 and 61 when the apparatus 10 is connected to the vertebrae 12 and 14. The disc 18 is inserted between the vertebrae 12 and 14 after the mounting members 100 are connected to the vertebrae. The ribs or guides 26 and 66 on opposite sides of the openings 36 and 70 of the disc 18 engage the mounting members 100 to guide the disc into a desired position between the vertebrae 12 and 14. The mounting members 100 are identical to each other. Accordingly, only one mounting member 100 will be described in detail.

The mounting member 100 (FIG. 5) is rigid and made of a biocompatible material such as a biocompatible metal or polymer. It is contemplated that the mounting member 100 could be made of a titanium alloy. The mounting member 100 has an outer surface 102 that faces the vertebra. An inner concave surface 104 of the mounting member 100 faces the resilient core 90. The inner concave surface 104 of the mounting member 100 of the upper retaining device 20 faces the upper surface 92 of the core 90. The inner concave surface 104 of the mounting member 100 of the lower retaining device 60 faces the lower surface 94 of the core 90.

The resilient core 90 deflects toward the concave surfaces 104 when a load is applied to the apparatus 10 to move the upper and lower retaining devices 20 and 60 relative to each other. The core 90 deflects into the openings 36 and 70 in the upper and lower retaining members 21 and 61 and into engagement with the concave surfaces 104 when the spine 16 is subject to a predetermined load, as shown in FIG. 7. When the core 90 engages the surfaces 104 of the mounting members 100, the resilient core stiffens since further deflection of the core toward the retaining devices 20 and 60 is restricted. It is contemplated that the retaining member 100 may have an axially extending opening to permit the escape of gas from between the core 90 and the mounting member.

The surfaces 104 of the mounting member 100 may have any desired configuration. The core 90 may engage different portions of the surfaces 104 as different loads are applied to the apparatus 10 to vary the stiffness of the core 90 at different loads. It is also contemplated that the surface 104 of the mounting member 100 of the retaining device 20 may have a different configuration than the surface 104 of the mounting member 100 of the retaining device 61.

Projections 106 extend from the outer surface 102 of the mounting member 100. The projections 106 engage the vertebrae 12 and 14 to help retain the apparatus 10 in position between the vertebra 12 and 14. Although the mounting member 100 is shown having four projections 106, it is contemplated that the mounting member may have any number of projections. It is contemplated that the projections 106 may have any desired shapes, sizes, and/or tip configurations. The projections 106 may include passages for bone ingrowth, have barbs, and/or have hooks.

The mounting member 100 includes a circular body 110 from which the projections 106 extend. Although the body 110 of the mounting member 100 is shown as being circular, it is contemplated that the body 110 may have any desired configuration that permits the mounting member 100 to slide into the openings 36 and 70 in the disc 18.

The body 110 of the mounting member 100 has a radially outer frustoconical surface 112. A rounded transition surface 113 extends from the radially outer surface 112 to the concave surface 104. The body 110 has a first diameter adjacent the outer surface 102 and a second diameter adjacent the transition surface 113 that is smaller than the first diameter. The radially outer surfaces 112 and/or the transition surfaces 113 of the mounting members 100 engage the ribs or guides 26 and 66 on the retaining members 21 and 61 to guide movement of the disc 18 in a first posterior direction relative to the mounting members and the vertebrae 12 and 14. The central ribs 28 and 68 on the upper and lower retaining members 21 and 61 act as stops to prevent movement of the disc 18 in the first direction after the disc has been inserted to a desired depth. The central ribs 28 and 68 engage the radially outer surfaces 112 and/or the transition surfaces 113 on the mounting member 100. When the central ribs 28 and 68 engage the mounting members 100, the radially outer surfaces 112 and/or the transition surfaces 113 guide relative movement between the mounting members and the retaining members 21 and 61 in second directions extending transverse to the first directions so that the mounting members move into the openings 36 and 70 in the disc 18.

The radially outer frustoconical surfaces 112 on the mounting members 100 engage the frustoconical surfaces 37 and 71 on the upper and lower retaining members 21 and 61 when the mounting members are in the openings 36 and 70 in the disc 18. The engagement of the surfaces 112 with the surfaces 37 and 71 creates interference fits between the mounting members 100 and the disc 18. Accordingly, the disc 18 is prevented from moving relative to the mounting members 100.

Figure 5:
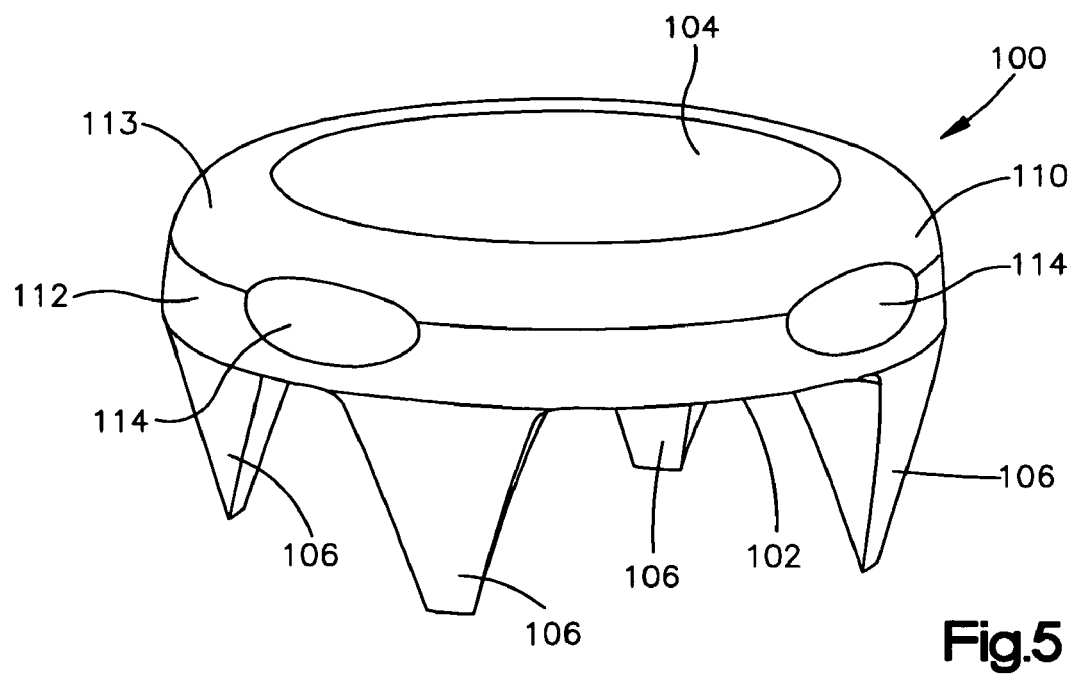
FIG. 5 is a pictorial view of a mounting member of the apparatus of FIG. 1.

The radially outer surface 112 has four recesses 114, two of which are shown in FIG. 5. The recesses 114 are located at 90° relative to each other. Although the mounting member 100 is described as having four recesses 114, it is contemplated that the mounting member 100 may have any number of recesses.

Figure 8:
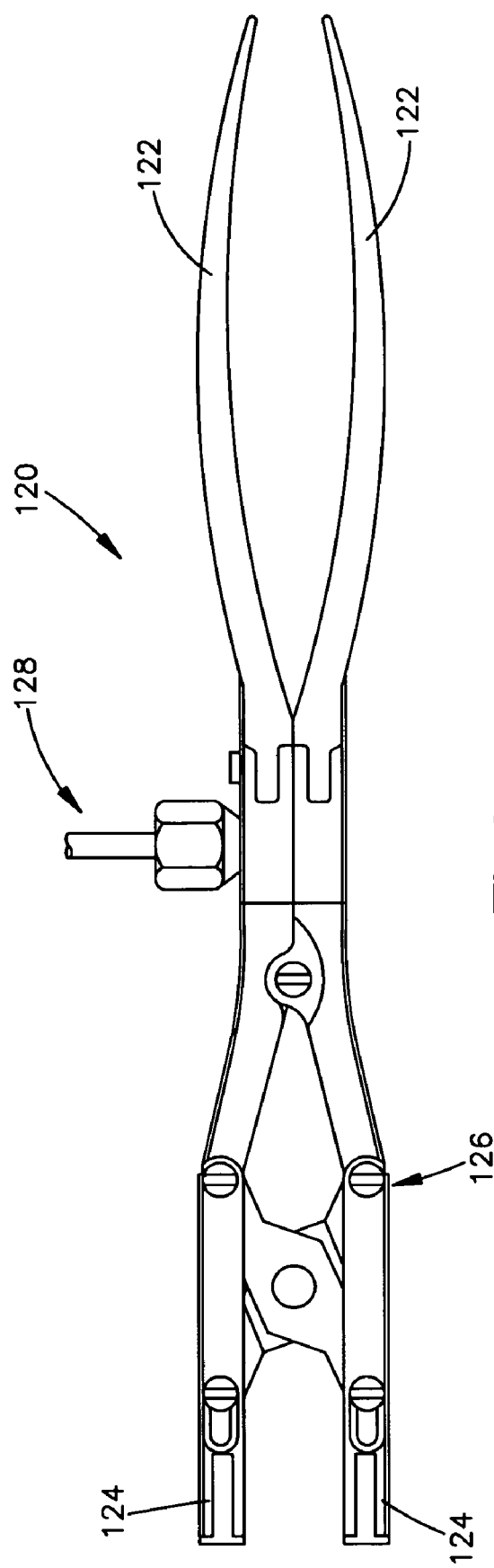
FIG. 8 is a schematic side view of an actuator for use in connecting mounting members shown in FIG. 5 to adjacent vertebrae.
Figure 9:
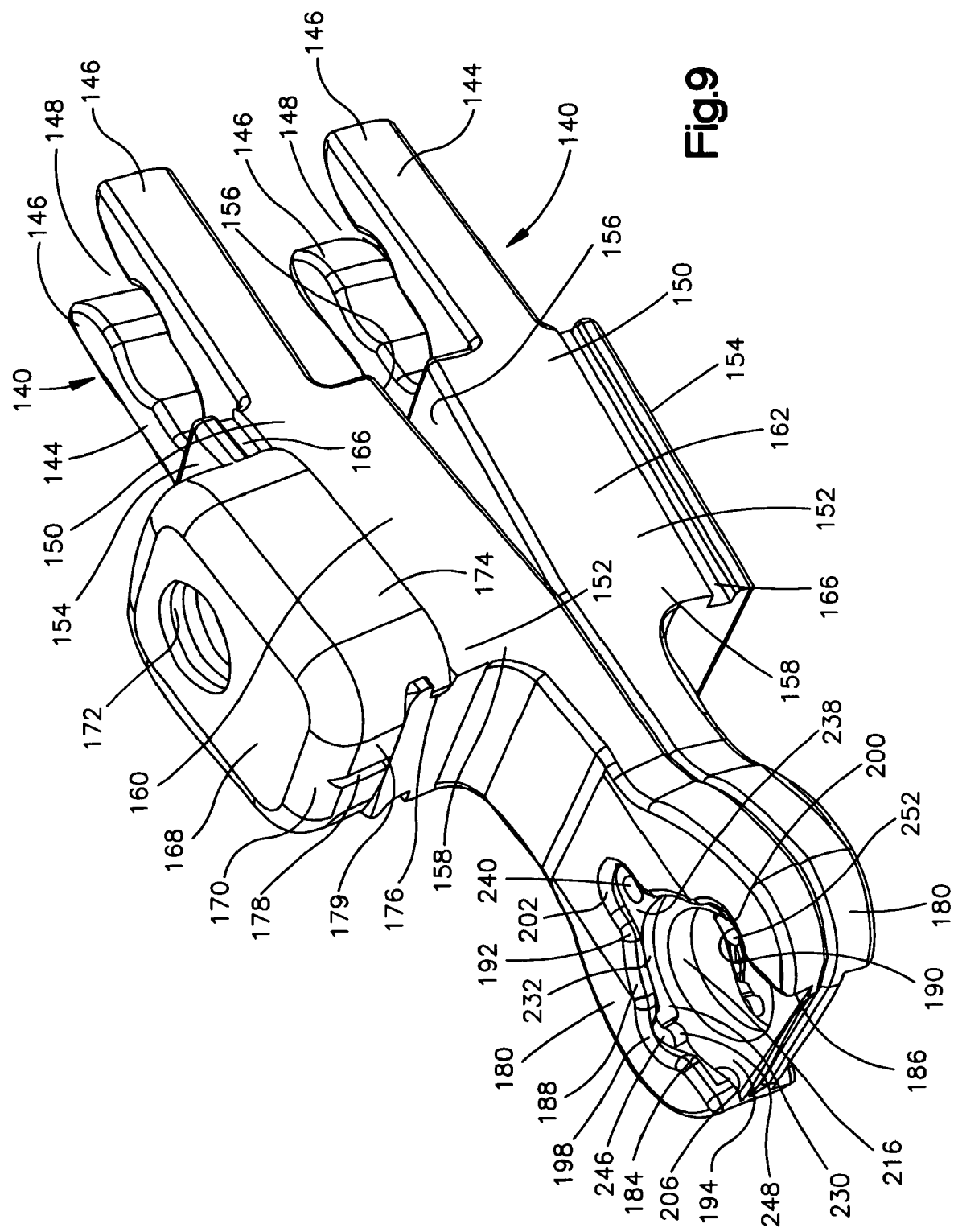
FIG. 9 is a pictorial view of insertion members for use with the actuator of FIG. 8 to connect the mounting members to adjacent vertebrae of the spinal column.
Figure 10:
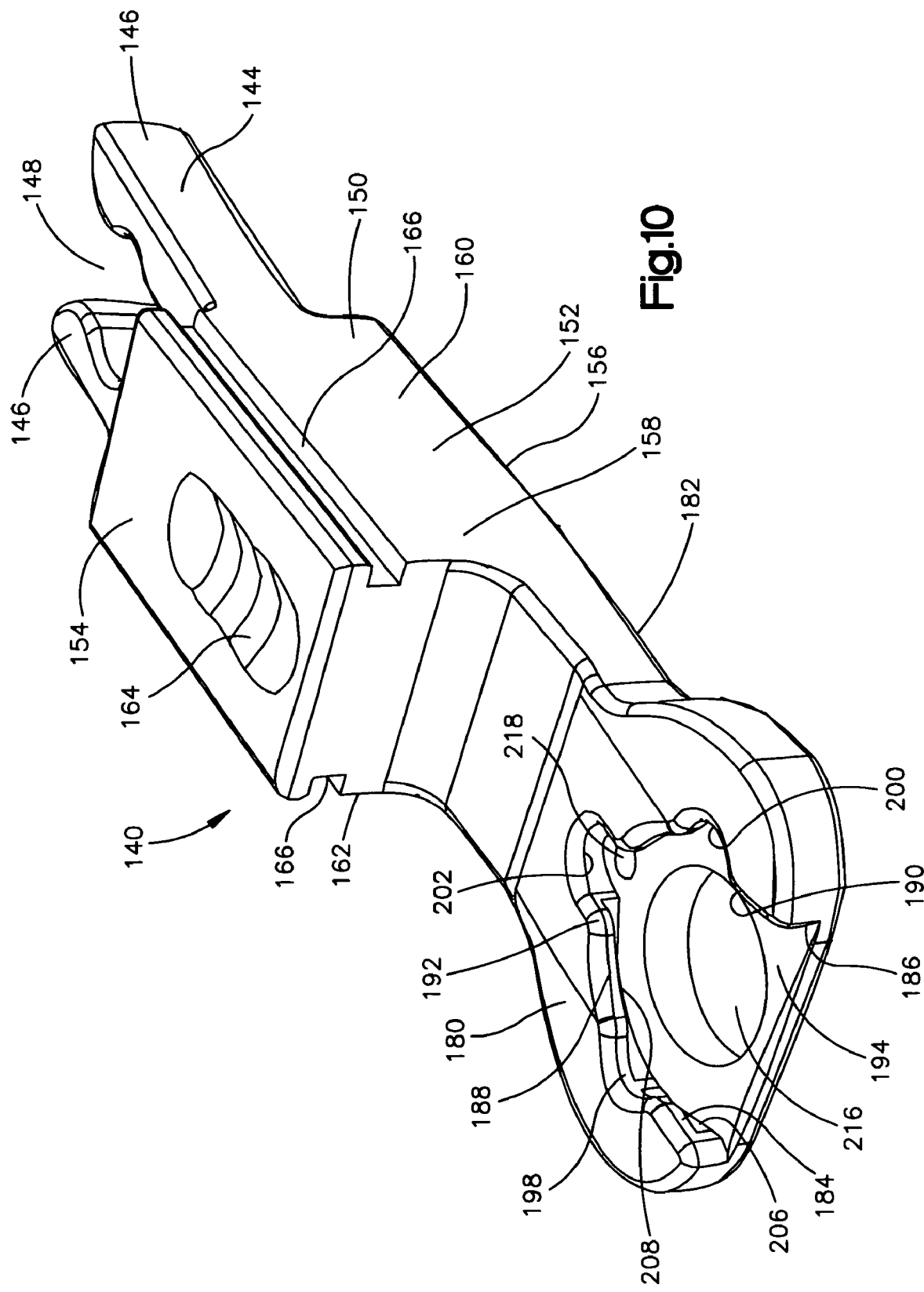
FIG. 10 is a pictorial view of one of the insertion members of FIG. 9.

The mounting members 100 may be connected to the vertebrae 12 and 14 using a surgical tool that includes an actuator 120 and a pair of insertion members 140 (FIGS. 8 and 9). The mounting members 100 are connected to the members 140 and the actuator 120 moves the members away from each other to connect the mounting members to the vertebrae. The actuator 120 (FIG. 8) may be a modular spine distractor manufactured by Friedrich GmbH of Solingen, Germany to which the members 140 are connected. The actuator 120 is known in the art and will not be described in detail.

The actuator 120 includes a pair of actuation handles 122 and a pair of separators 124 that are connectable to the members 140. The handles 122 are connected to the separators 124 by a linkage system 126. Upon movement of the handles 122 toward each other, the linkage system 126 causes the separators 124 to move away from each other. The actuator 120 also includes a locking mechanism 128 for locking the separators 124 at a desired distance from each other.

The insertion members 140 (FIGS. 9-13) are connectable to the separators 124. The members 140 are identical to each other. Accordingly, only one member 140 will be described in detail.

The member 140 includes a connecting end 144 that is insertable into an opening (not shown) in one of the separators 124 of the actuator 120. The end 144 includes a pair of projections 146. The projections 146 (FIG. 12) extend generally parallel to each other and define a channel 148 between them. The end 144 is inserted into the opening (not shown) in the separator 124 of the actuator 120 to connect the member 140 to the actuator in a known manner. The member 140 may be removed from the separator 124 in a known manner. It is contemplated that the end 144 of the member 140 hay have any desired configuration to connect the member to a desired actuator.

The projections 146 (FIGS. 9-12) extend from a first end 150 of a central body 152 of the member 140. The central body 152 has an upper surface 154 and a parallel lower surface 156 extending from the first end 150 to a second end 158 of the central body. The projections 146 extend at an angle to the surfaces 154 and 156. It is contemplated that the projections 146 may extend at any desired angle to the surfaces 154 and 156. The upper surface 154 has a scalloped recess 164.

Side surfaces 160 and 162 extend from the upper surface 154 to the lower surface 156. A pair of longitudinally extending grooves 166 (FIG. 10) located in the side surfaces 160 and 162 extend along the body 152. The grooves 166 extend from the first end 150 to the second end 158.

Figure 14:
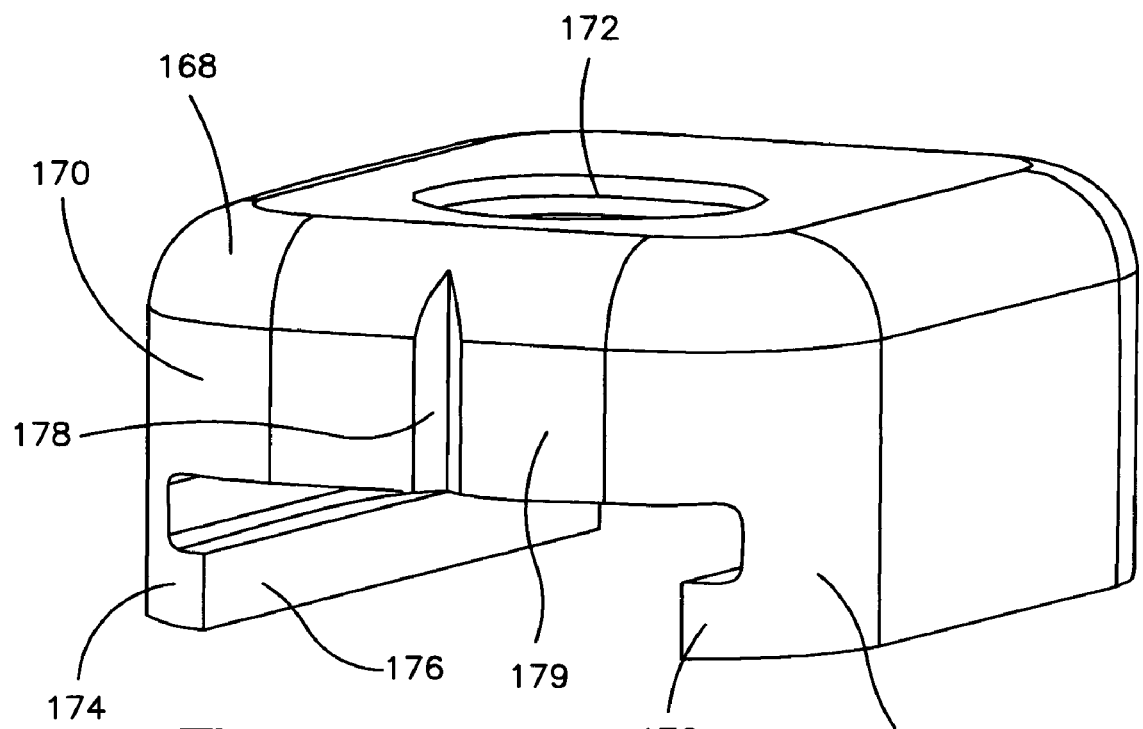
FIG. 14 is a pictorial view of a slider connectable to one of the insertion members of FIG. 9.

A slider 168 (FIGS. 9 and 14) may be connected to the body 152 of the member 140. The slider 168 engages one of the vertebrae 12 and 14 to prevent further insertion of the mounting members 100 in the proximal direction between the vertebrae. The slider 168 includes a main body portion 170 with a threaded opening 172. A pair of flanges 174 extend downwardly from the body portion 170. The flanges 174 (FIG. 14) extend generally parallel to each other and include portions 176 extending toward each other. The portions 176 are received in the grooves 166 in the body 152 of the member 140. The slider 168 includes a vertically extending groove 178 in a surface 179 that faces away from the connecting end 144 of the member 140.

The slider 168 may be moved relative the body 152 toward and away from the end 144 of the member 140. A set screw (not shown) is threaded into the opening 172 and extends into the scalloped recess 164 to prevent movement of the slider 168 relative to the body 152. The scalloped recess 164 defines a plurality of positions for the slider 168 relative to the member 140.

An insertion end 180 (FIGS. 9-13) of the member 140 extends from the second end 158 of the body 152. The insertion end 180 extends at an angle to the upper and lower surfaces 154 and 156 of the body 152 and generally parallel to the projections 146. It is contemplated that the insertion end 180 may extend at any desired angle relative to the surfaces 154 and 156. The insertion end 180 (FIG. 11) has a lower surface 182 that extends at an angle to the lower surface 156 of the body 152.

The insertion end 180 (FIG. 12) includes a recess 184 for receiving the mounting member 100. The recess 184 is generally U-shaped with an open end 186 through which the mounting member 100 may be inserted into the recess and removed from the recess. The recess 184 is defined by sidewalls 188 and 190 interconnected by a back wall 192. A bottom wall 194 extends generally perpendicular to the sidewalls 188 and 190 and the back wall 192.

The sidewall 188 has a notch 198 extending radially outwardly. The sidewall 190 includes a notch 200 extending radially outwardly. The back wall 192 has a notch 202 extending toward the body 152. A groove 206 (FIGS. 10 and 13) is formed in the sidewall 188 extending from adjacent the open end 186 to the notch 198. A groove 208 extends from the notch 198 to the notch 202. A groove (not shown) similar to the groove 208 extending between the notch 202 and the notch 200 is formed in the sidewall 190. Another groove (not shown) similar to the groove 206 extending from the notch 200 to adjacent the open end 186 is formed in the sidewall 190.

A first circular opening 216 extends through the bottom wall 194 and is centrally located in the recess 184. The opening 216 permits removal of the mounting member 100 from the recess 184 if needed. A second smaller circular opening 218 extends through the bottom wall 194 and is located in the notch 202.

Figure 15:
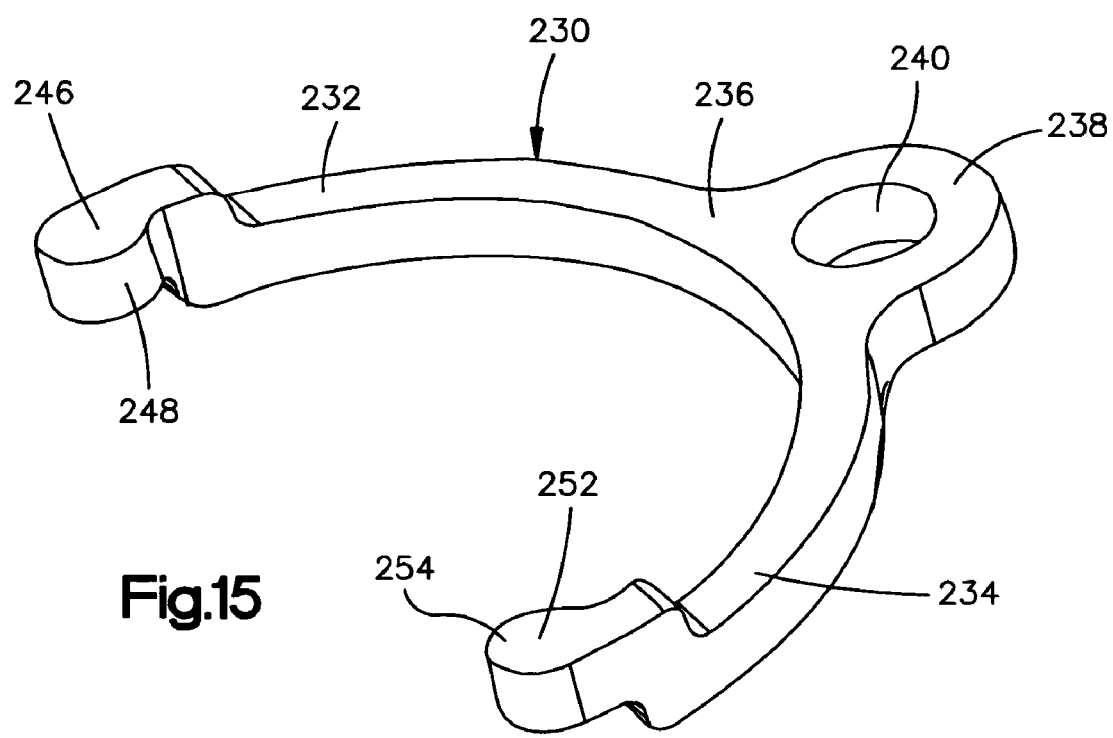
FIG. 15 is a pictorial view of a spring member for connecting the mounting member to one of the insertion members of FIG. 9.

A spring member 230 (FIGS. 9 and 15) is received in the recess 184 to hold the mounting member 100 in the recess. The spring member 230 is generally U-shaped and includes a pair of arms 232 and 234 extending from a base 236. A projection 238 extends from the base 236 in a direction opposite from the arms 232 and 234. The projection 238 has a circular opening 240 for receiving a pin (not shown) to connect the spring member 230 to the member 140. The pin (not shown) extends through the opening 240 in the spring member 230 and into the opening 218 in the member 140 to connect the spring member to the member 140.

The arm 232 includes an upwardly extending end 246 that engages the mounting member 100 to retain the mounting member in the member 140. The end 246 has a radially inwardly extending projection 248. The projection 248 extends into one of the recesses 114 in the mounting member 100 to retain the mounting member in the member 140.

The arm 234 has an upwardly extending end 252. The end 252 has a radially inwardly extending projection 254. The projection 254 extends into one of the recesses 114 in the mounting member 100 to retain the mounting member in the member 140.

The spring member 230 is inserted into the recess 184 through the open end 186. The arms 232 and 234 extend into the groove 206 in the sidewall 188 and the groove (not shown) in the sidewall 190 extending from the notch 200 to adjacent the open end 186, as the spring 230 is being inserted into the recess 184. The ends 246 and 252 of the arms 232 and 234 move toward each other. When the ends 246 and 252 are adjacent the notches 198 and 200, the ends 246 and 252 move away from each other.

When the spring 230 (FIG. 9) is inserted in the recess 184, the arm 232 extends into the groove 208 and the arm 234 extends into the groove (not shown) extending from the notch 202 to the notch 200 in the insertion end 180 of the member 140. The opening 240 in the projection 238 of the spring member 230 is aligned with the opening 218 in the insertion end 180. A pin (not shown) extends through the opening 240 in the spring member 230 and into the opening 218 to retain the spring member in the recess 184. The ends 246 and 252 extend upwardly into the notches 198 and 200 in the sidewalls 188 and 190.

Upon insertion of the mounting member 100 between the ends 246 and 252 of the spring 230, the ends move radially outwardly away from each other into the notches 198 and 200 until the recesses 114 are aligned with the projections 248 and 254. When the recesses 114 are aligned with the projections 248 and 254, the ends 246 and 252 move toward each other into the recesses to retain the mounting member 100 in the insertion end 180. The mounting member 100 may be removed from the recess 184 by overcoming the retaining force applied by the spring member 230.

An insertion tool 300 for inserting the disc 18 between the vertebrae 12 and 14 after the mounting members 100 are connected to the vertebrae 12 and 14 is illustrated in FIGS. 16 and 17. The tool 300 (FIG. 16) resembles a common pair of scissors and has a pair of legs 302 and 304 pivotally connected to one another. The tool 300 includes a grasping end 306 formed by a pair of jaws 308 on the legs 302 and 304. The jaws 308 (FIG. 17) include oval shaped projections 310 extending toward each other. The projections 310 are inserted into the openings 48 and 82 in the disc 18 to grasp the disc for insertion between the vertebrae 12 and 14.

The leg 302 (FIG. 15) has an enlarged end 312 opposite the jaw 308. The enlarged end 312 may be struck with a mallet to drive the disc 18 between the vertebrae 12 and 14 if needed. The leg 304 has a curved handle 314 opposite the jaw 308. The handle 314 is easily grasped by a surgeon for manipulating the tool 300.

A locking mechanism 320 prevents the jaws 308 from pivoting away from each other after the projections 310 have been inserted into the openings 48 and 82 in the disc 18. The locking mechanism 320 includes a rod 322 pivotally connected to a mounting portion 324 extending from the leg 304. The rod 322 has a threaded end 326 that extends through an opening 328 in the leg 302. A nut 332 threadably engages the end 326 of the rod 322 and engages the leg 302 to prevent the jaws 308 from pivoting away from each other.

When the apparatus 10 is to be inserted between the vertebrae 12 and 14, an anterior space adjacent the vertebrae is exposed using a retroperitoneal or transperitoneal approach. A midline reference is established. A midline marker, such as a K-wire, is placed to maintain a reference point to the center of one of the vertebrae 12 and 14. The space between the vertebrae 12 and 14 is distracted and the damaged disc between the vertebrae is excised. After the damaged disc is excised, the cartilaginous end plates are removed from the vertebrae 12 and 14. The vertebrae 12 and 14 are then sculpted as desired.

The appropriate size apparatus 10 is determined by using trial sizers. The trial sizers are similar to the disc 18. The trial sizers are inserted between the vertebrae 12 and 14 to determine the desired footprint, wedge angle, and disc height needed to replace the excised disc. The desired footprint, wedge angle and disc height are confirmed using fluoroscopy.

The mounting members 100 are then inserted into the vertebrae 12 and 14. The appropriate members 140 are selected based upon the desired wedge angle for use between the vertebrae 12 and 14. The mounting members 100 are inserted into the recesses 184 in the member 140. The insertion ends 180 of the members 140 are inserted between the vertebrae 12 and 14 until the midline marker extends into the groove 178 on the slider 168 and the slider 168 engages the anterior ridge of one of the vertebrae 12 and 14 directly under the midline marker. Once the insertion ends 180 of the members 140 have been inserted into the desired depth, the insertion ends are moved away from each other by the actuator 120 to insert the projections 106 on the mounting members 100 into the vertebrae 12 and 14. After the mounting members 100 have been connected to the vertebrae 12 and 14, the members 140 are removed from between the vertebrae 12 and 14 leaving the mounting members behind.

After the mounting members 100 are connected to the vertebrae 12 and 14, a trial sizer may be reinserted between the vertebrae. Verification of the position of the trial sizer is achieved using fluoroscopy. If it is determined that the mounting members 100 are not in the desired positions, the mounting members can be easily removed and repositioned in the vertebrae.

After the mounting members 100 are connected to the vertebrae 12 and 14 in their desired positions, the insertion tool 300 is connected with the disc 18. The disc 18 is then inserted between the vertebrae 12 and 14. During insertion of the disc 18, the ribs 26 and 66 on opposite sides of the openings 36 and 70 engage the surfaces 112 and 113 on the mounting members 100 to guide insertion of the disc. The central ribs 28 and 68 engage the mounting members 100 when the disc 18 has been inserted to the desired depth between the vertebrae 12 and 14. The ribs 26, 28, 66, and 68 on the disc 18 guide insertion of the mounting members 100 into the openings 36 and 70 in the disc 18.

After the disc 18 is placed into the desired position between the vertebrae 12 and 14, the tool 300 is removed from the disc. The ribs 26, 28, 66 and 68 on the disc 18 engage the vertebrae 12 and 14 when the mounting members 100 are inserted in the openings 36 and 70 in the disc 18. The mounting members 100 and ribs 26, 28, 66 and 68 retain the apparatus 10 in position between the vertebrae 12 and 14.

When the apparatus 10 is in use in the spinal column 16, the upper retaining device 20 is affixed to the vertebra 12. The ribs 26 and 28 and the projections 106 on the mounting member 100 resist relative movement between the upper retaining device 20 and vertebra 12. The lower retaining device 60 is affixed to the vertebra 14. The ribs 66 and 68 and the projections 106 on the mounting member 100 resist relative movement between the lower retaining device 60 and the vertebra 14.

When the upper and lower retaining devices 20 and 60 move relative to each other, such as when the spine 16 is in compression, as shown in FIG. 7, the resilient core 90 deflects toward the concave surfaces 104 on the mounting members 100. The resilient core 90 also deflects toward the surfaces 52 and 86 on the retaining members 21 and 61 when a load is applied to the apparatus. Accordingly, the core 90 expends energy to reduce stress in the core upon relative movement of the upper and lower retaining devices 20 and 60 to provide a relatively long fatigue life for the apparatus 10.

The resilient core 90 deflects into engagement with the surfaces 104 of the mounting members 100 when a predetermined load is applied. The core 90 also deflects into engagement with the surfaces 52 and 86 on the retaining members 21 and 61 when a predetermined load is applied. Accordingly, the core 90 stiffens when the core engages the surfaces 104, 52, and 86 since further deflection of the core is restricted. It is contemplated that the core 90 may engage the surfaces 104, 52, and 86 at different applied loads.

Although the ribs 26 and 66 on the disc 18 are described as engaging the mounting members 100 to guide insertion of the disc between the vertebrae 12 and 14, it is contemplated that the mounting members 100 may have grooves that ribs on the disc 18 extend into to guide insertion of the disc. It is also contemplated that the mounting members 100 may have ribs that extend into grooves in the disc 18 to guide insertion of the disc. Furthermore, it is contemplated that the disc 18 may be inserted between the vertebrae 12 and 14 without use of the mounting members 100. If the disc 18 is used without the mounting members 100, it is contemplated that the retaining members 21 and 61 of the retaining devices 20 and 60 would include inner concave surfaces similar to the inner concave surfaces 104 of the mounting members. The core 90 would be spaced from the inner concave surfaces on the retaining members 21 and 61 and deflect into engagement with the inner concave surfaces when a predetermined load was applied to the apparatus 10.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, we claim:

1. A method for replacing a damaged spinal disc between first and second vertebrae of a spinal column comprising:

connecting a first mounting member with the first vertebra of the spinal column; and moving an artificial disc between the first and second vertebrae and into engagement with the first mounting member to guide the artificial disc into position between the first and second vertebrae, the artificial disc including a resilient core having a first surface and a second surface, a first retaining member fixedly connected to the first surface of the resilient core, and a second retaining member fixedly connected to the second surface of the resilient core, the first retaining member having an outer surface directly engageable with the first vertebra of the spinal column after the artificial disc is in position between the first and second vertebrae and an inner surface facing the first surface of the resilient core, the second retaining member having an outer surface directly engageable with the second vertebra of the spinal column after the artificial disc is in position between the first and second vertebrae and an inner surface facing the second surface of the resilient core.

2. A method as defined in claim 1 further including engaging the first mounting member with a guide on the first retaining member to guide movement of the first retaining member into position between the first and second vertebrae.

3. A method as defined in claim 2 wherein said step of engaging the first mounting member with the guide on the first retaining member includes engaging the first mounting member with a guide extending from the outer surface of the first retaining member and engaging the first vertebra with the guide.

4. A method as defined in claim 1 further including engaging the first mounting member with first and second guides extending generally parallel to each other on the first retaining member to guide movement of the first retaining member into position between the first and second vertebrae.

5. A method as defined in claim 1 further including engaging the first mounting member with a stop on the first retaining member to prevent relative movement between the first retaining member and the first mounting member in a first direction.

6. A method as defined in claim 5 further including guiding movement of the first retaining member relative to the first mounting member in a second direction extending transverse to the first direction.

7. A method as defined in claim 1 further including guiding movement of the first mounting member into an opening in the first retaining member.

8. A method as defined in claim 1 wherein the step of connecting the first mounting member with the first vertebra includes engaging the first mounting member with a surgical tool for connecting the first mounting member to the first vertebra.

9. A method as defined in claim 8 wherein the step of engaging the first mounting member with the surgical tool includes extending a portion of the surgical tool into a recess in the first mounting member.

10. A method as defined in claim 1 further including spacing an inner surface of the first mounting member that faces the core from the core.

11. A method as defined in claim 1 further including connecting the artificial disc to the first mounting member.

12. A method as defined in claim 11 wherein the step of connecting the artificial disc to the first mounting member includes preventing movement of the first mounting member relative to the artificial disc.

13. A method as defined in claim 12 wherein the step of preventing movement of the first mounting member relative to the artificial disc includes connecting the artificial disc to the first mounting member with an interference fit.

14. A method as defined in claim 13 wherein the step of connecting the artificial disc to the first mounting member with an interference fit includes engaging a frustoconical surface on the artificial disc with a frustoconical surface on the first mounting member.

15. A method as defined in claim 1 further including connecting a second mounting member to the second vertebra, said step of moving the artificial disc between the first and second vertebrae including engaging the second mounting member with the artificial disc to guide movement of the artificial disc into position between the first and second vertebrae.

16. A method as defined in claim 15 further including engaging the first mounting member with a first guide on the first retaining member to guide movement of the first retaining member into position between the first and second vertebrae and engaging the second mounting member with a second guide on the second retaining member to guide movement of the second retaining member into position between the first and second vertebrae.

17. A method as defined in claim 16 wherein the step of engaging the first mounting member with the first guide on the first retaining member includes engaging the first mounting member with the first guide extending from the outer surface of the first retaining member and engaging the first vertebra with the first guide, the step of engaging the second mounting member with the second guide on the second retaining member including engaging the second mounting member with the second guide extending from the outer surface of the second retaining member and engaging the second vertebra with the second guide.

18. A method as defined in claim 15 further including engaging the first mounting member with first and second guides extending generally parallel to each other on the first retaining member to guide movement of the first retaining member into position between the first and second vertebrae, and engaging the second mounting member with third and fourth guides extending generally parallel to each other on the second retaining member to guide movement of the second retaining member into position between the first and second vertebrae.

19. A method as defined in claim 15 further including engaging the first mounting member with a first stop on the first retaining member to prevent relative movement between the first retaining member and the first mounting member in a first direction and engaging the second mounting member with a second stop on the second retaining member to prevent relative movement between the second retaining member and the second mounting member in the first direction.

20. A method as defined in claim 19 further including guiding movement of the first retaining member relative to the first mounting member in a direction extending transverse to the first direction and guiding movement of the second retaining member relative to the second mounting member in a direction extending transverse to the first direction.

21. A method as defined in claim 15 further including guiding movement of the first mounting member into an opening in the first retaining member and guiding movement of the second mounting member into an opening in the second retaining member.

22. A method as defined in claim 15 wherein the step of connecting the first mounting member with the first vertebra includes connecting the first mounting member with a surgical tool for connecting the first mounting member to the first vertebra, the step of connecting the second mounting member with the second vertebra including connecting the second mounting member with the surgical tool for connecting the second mounting member to the second vertebra.

23. A method as defined in claim 22 further including moving the first and second mounting members away from each other to connect the first and second mounting members to the first and second vertebrae.

24. A method as defined in claim 22 wherein the step of connecting the first mounting member with the surgical tool includes extending a first portion of the surgical tool into a recess in the first mounting member, the step of connecting the second mounting member with the surgical tool including extending a second portion of the surgical tool into a recess in the second mounting member.

25. A method as defined in claim 15 further including spacing an inner surface of the first mounting member that faces the core from the core and spacing an inner surface of the second mounting member that faces the core from the core.

26. A method as defined in claim 15 further including connecting the artificial disc to the first and second mounting members.

27. A method as defined in claim 26 wherein the step of connecting the artificial disc to the first and second mounting members includes preventing movement of the first and second mounting members relative to the artificial disc.

28. A method as defined in claim 27 wherein the step of preventing movement of the first and second mounting members relative to the artificial disc includes connecting the artificial disc to the first and second mounting members with interference fits.

29. A method as defined in claim 28 wherein the step of connecting the artificial disc to the first and second mounting members with interference fits includes engaging frustoconical surfaces on the artificial disc with frustoconical surfaces on the first and second mounting members.

30. A method as defined in claim 1 wherein the step of moving the artificial disc between the first and second vertebrae includes connecting a surgical tool to a first portion of the first retaining member.

31. A method as defined in claim 30 wherein the step of moving the artificial disc between the first and second vertebrae includes connecting the surgical tool to a first portion of the second retaining member.

32. A method as defined in claim 31 wherein the step of connecting the surgical tool to the first portion of the first retaining member includes extending a first portion of the surgical tool into a first opening in the first portion of the first retaining member.

33. A method as defined in claim 32 wherein the step of connecting the surgical tool to the first portion of the second retaining member includes extending a second portion of the surgical tool into a first opening in the first portion of the second retaining member.

34. A method for replacing a damaged spinal disc between first and second vertebrae of a spinal column comprising:

connecting a first mounting member with the first vertebra of the spinal column;

moving an artificial disc between the first and second vertebrae and into engagement with the first mounting member to guide the artificial disc into position between the first and second vertebrae, the artificial disc including a resilient core having a first surface and a second surface, a first retaining member connected to the first surface of the resilient core, and a second retaining member connected to the second surface of the resilient core, the first retaining member having an outer surface engageable with the first vertebra of the spinal column and an inner surface facing the first surface of the resilient core, the second retaining member having an outer surface engageable with the second vertebra of the spinal column and an inner surface facing the second surface of the resilient core; and engaging the first mounting member with a guide extending from the outer surface of the first retaining member to guide movement of the first retaining member into position between the first and second vertebrae and engaging the first vertebra with the guide.

35. A method as defined in claim 34 further including engaging the first mounting member with first and second guides extending generally parallel to each other on the first retaining member to guide movement of the first retaining member into position between the first and second vertebrae.

36. A method as defined in claim 34 further including connecting a second mounting member to the second vertebra, said step of moving the artificial disc between the first and second vertebrae including engaging the second mounting member with the artificial disc to guide movement of the artificial disc into position between the first and second vertebrae.

37. A method as defined in claim 36 further including engaging the second mounting member with a second guide on the second retaining member to guide movement of the second retaining member into position between the first and second vertebrae.

38. A method as defined in claim 37 wherein the step of engaging the second mounting member with the second guide on the second retaining member includes engaging the second mounting member with the second guide extending from the outer surface of the second retaining member and engaging the second vertebra with the second guide.

39. A method as defined in claim 36 further including engaging the first mounting member with first and second guides extending generally parallel to each other on the first retaining member to guide movement of the first retaining member into position between the first and second vertebrae, and engaging the second mounting member with third and fourth guides extending generally parallel to each other on the second retaining member to guide movement of the second retaining member into position between the first and second vertebrae.

* * * * *

UNITED STATES PATENT AND TRADEMARK OFFICE
CERTIFICATE OF CORRECTION

PATENT NO. : 7,588,600 B2 Page 1 of 1
APPLICATION NO. : 10/731942
DATED : September 15, 2009
INVENTOR(S) : Benzel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1573 days.

Signed and Sealed this

Twenty-first Day of September, 2010

David J. Kappos
*Director of the United States Patent and Trademark Office*